United States Patent
Siegel et al.

(10) Patent No.: US 7,925,326 B2
(45) Date of Patent: Apr. 12, 2011

(54) SOLID FIDUCIARY MARKER FOR MULTIMODALITY IMAGING

(75) Inventors: Stefan Siegel, Knoxville, TN (US); Eric Arnsdorff, Knoxville, TN (US); Xinli Liu, Knoxville, TN (US)

(73) Assignee: Siemens Molecular Imaging, Inc., Knoxville, TN (US)

( * ) Notice: Subject to any disclaimer, the term of this patent is extended or adjusted under 35 U.S.C. 154(b) by 1167 days.

(21) Appl. No.: 11/219,372

(22) Filed: Sep. 2, 2005

(65) Prior Publication Data

US 2007/0073143 A1    Mar. 29, 2007

Related U.S. Application Data

(60) Provisional application No. 60/607,152, filed on Sep. 3, 2004.

(51) Int. Cl.
*A61B 5/00* (2006.01)

(52) U.S. Cl. ........ 600/414; 600/411; 600/426; 600/427; 600/436; 600/476

(58) Field of Classification Search .................. 600/411, 600/414, 426, 427, 436, 476; 378/204
See application file for complete search history.

(56) References Cited

U.S. PATENT DOCUMENTS

| | | | | |
|---|---|---|---|---|
| 4,233,507 A | * | 11/1980 | Volz | 378/18 |
| 4,922,915 A | * | 5/1990 | Arnold et al. | 382/128 |
| 5,178,146 A | * | 1/1993 | Giese | 600/411 |
| 5,211,166 A | * | 5/1993 | Sepponen | 600/420 |
| 5,817,017 A | * | 10/1998 | Young et al. | 600/433 |
| 6,484,049 B1 | * | 11/2002 | Seeley et al. | 600/426 |
| 2004/0167393 A1 | * | 8/2004 | Solar et al. | 600/414 |

* cited by examiner

*Primary Examiner* — Ruth S Smith
(74) *Attorney, Agent, or Firm* — Peter L. Kendall

(57) ABSTRACT

A solid fiduciary marker for registering at least two images when imaging the same subject using distinct imaging devices is disclosed. The solid fiduciary marker is visible in at least two of a Positron Emission Tomography (PET), Single Photon Emission Computed Tomography (SPECT), Planar gamma camera, X-ray CT, planar X-ray, Magnetic Resonance Imaging (MRI), and optical imager. The marker includes at least two of various doping compounds to be detected by the various imaging systems. The doping compounds include a positron emitting nuclide, a gamma emitting nuclide, a doping compound, metal, and a silicone-based polymer is used in association with an MRI device.

10 Claims, 2 Drawing Sheets

SOLID FIDUCIARY MARKER FOR MULTIMODALITY IMAGING

CROSS-REFERENCE TO RELATED APPLICATIONS

This application claims the benefit of U.S. Provisional Application No. 60/607,152, filed Sep. 3, 2004.

STATEMENT REGARDING FEDERALLY SPONSORED RESEARCH OR DEVELOPMENT

Not Applicable

BACKGROUND OF THE INVENTION

1. Field of Invention

The present invention pertains to the field of imaging. More particularly, this invention is directed toward a solid fiduciary marker that can be molded into a desired shape and is detectable in a plurality of imaging modalities including, but not limited to, Nuclear Medicine such as Positron Emission Tomography (PET), Single Photon Emission Computed Tomography (SPECT), including planar modalities; Radiology such as X-Ray Computed Tomography (CT), also including planar modalities; Magnetic Resonance Imaging (MRI); and optical imaging.

2. Description of the Related Art

Image registration has been a topic with much interest. It has many applications including, but not limited to, radiotherapy, functional imaging, and molecular imaging. Having fixed fiducial markers not only permits rigid, inelastic, registration of the images, but also provides true mutual information markers that can guide elastic transformation between devices, between subjects and even to generic topologies such as Tailerac maps.

The new markers have a practical lifetime of over one (1) year. Accordingly, they may be affixed to restraint devices and beds for use in multiple studies. Further, because the doping concentration is controlled and because of their small size, the markers may be embedded in molded fixation devices used with specific subjects or patients. Thus, the markers may be used in radiotherapy protocols which require tight control of the treatment beam. After therapy has been completed, the markers may be salvaged or discarded. The same molded fixation device may be used when longitudinal PET, SPECT, CT and/or MRI studies are to be done on the same subject.

Current technology relies on non-reusable liquid filled markers to achieve registration across various imaging modes. In order to obtain nuclear medicine images with current technology, the marker must be injected with a liquid containing the appropriate nuclide and this represents a contamination hazard. This methodology limits the size and shape of the marker and presents problems in determining the precise marker location. This methodology also limits the amount of time between studies due to its disposable single use construction and short-lived isotopes.

A sample of a current commercial marker is that manufactured by IZI Medical Products. In order to achieve registration for nuclear imaging the product must be injected with a short-lived liquid based nuclide.

BRIEF SUMMARY OF THE INVENTION

A solid fiduciary marker for registering at least two images when imaging the same subject using distinct imaging devices is disclosed. The solid fiduciary marker is a semi-permanent marker with properties which make it visible in at least two of the following imaging devices: Positron Emission Tomography (PET), Single Photon Emission Computed Tomography (SPECT), Planar gamma camera, X-ray CT, planar X-ray, Magnetic Resonance Imaging (MRI), and optical imagers. The marker is formed into virtually any shape.

The marker is a silicone-based polymer doped with at least two of various doping compounds to be detected by the various imaging systems. The doping compound for use with a PET scanner is a positron emitting nuclide. A gamma emitting nuclide is used as the doping compound for use with either of a SPECT or planar gamma camera. The doping compound used in association with X-ray CT or planar X-ray is metal. A silicone-based polymer is used in association with an MRI device. Finally, for an optical imager, the doping compound is a photostimulable phosphor.

In one embodiment, a bed or other fixation device is used for each of the selected imaging devices. For example, a patient bed is configured to be received within the imaging gantry of both the PET device and the MRI device. The marker is contained in or attached to the bed as desired for the particular implementation. The patient is then placed on the patient bed. The patient bed is then moved into each of the PET and MRI devices sequentially, while the patient remains on the patient bed. The resulting images thus include data from both the patient and the marker. Because the relative position of the marker with respect to the patient is the same in both images, the registration as described above yields more of a complete image of both the soft tissue and bones of the patient.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

The present invention is a solid fiduciary marker for registering at least two images when imaging the same subject using distinct imaging devices. The solid fiduciary marker, illustrated at 12 in the figures, is a semi-permanent marker with properties which make it visible in at least two of the following imaging devices: Positron Emission Tomography (PET), Single Photon Emission Computed Tomography (SPECT), Planar gamma camera, X-ray CT, planar X-ray, Magnetic Resonance Imaging (MRI), and optical imagers. The marker 12 is formed into virtually any shape. The size of the marker 12 may be made small enough to provide "point" locations for image registration.

The marker 12 is constructed in various geometries to meet many research and diagnostic needs. The marker 12 is a doped silicone-based polymer. The doping compounds add to the ability to be detected by the various imaging systems. The doping compound for use with a PET scanner is a positron emitting nuclide. A gamma emitting nuclide is used as the doping compound for use with either of a SPECT or planar gamma camera. The doping compound used in association with X-ray CT or planar X-ray is metal. A silicone-based polymer is used in association with an MRI device. Finally, for an optical imager, the doping compound is a photostimulable phosphor.

In order to register the marker 12 in more than one modality, the respective dopants are added to the material of manufacture. For example, a marker fabricated for use with both a PET device and an MRI device, the marker 12 is doped with positron emitting nuclides as well as a silicone-based polymer. The marker is then placed within the geometry of each of the PET and MRI devices at the same relative location to the patient. After the individual scans are performed and data collected, the data from the marker in each scan are registered, thereby registering all of the data from both scans.

In one embodiment, a bed 18 or other fixation device is used for each of the selected imaging devices 14. In the above example, a patient bed 18 is configured to be received within the imaging gantry 16 of both the PET device and the MRI device. The marker 12 is contained in or attached to the bed 18 as desired for the particular implementation. The patient is then placed on the patient bed 18. The patient bed 18 is then moved into each of the PET and MRI devices 14 sequentially, while the patient remains on the patient bed 18. The resulting images thus include data from both the patient and the marker 12. Because the relative position of the marker 12 with respect to the patient is the same in both images, the registration as described above yields more of a complete image of both the soft tissue and bones of the patient.

The material use to fabricate the marker 12 is moldable into shapes for calibration devices used on the various imaging cameras. The marker 12 is moldable into human or animal organ shapes and used for various research studies.

Figure 1:
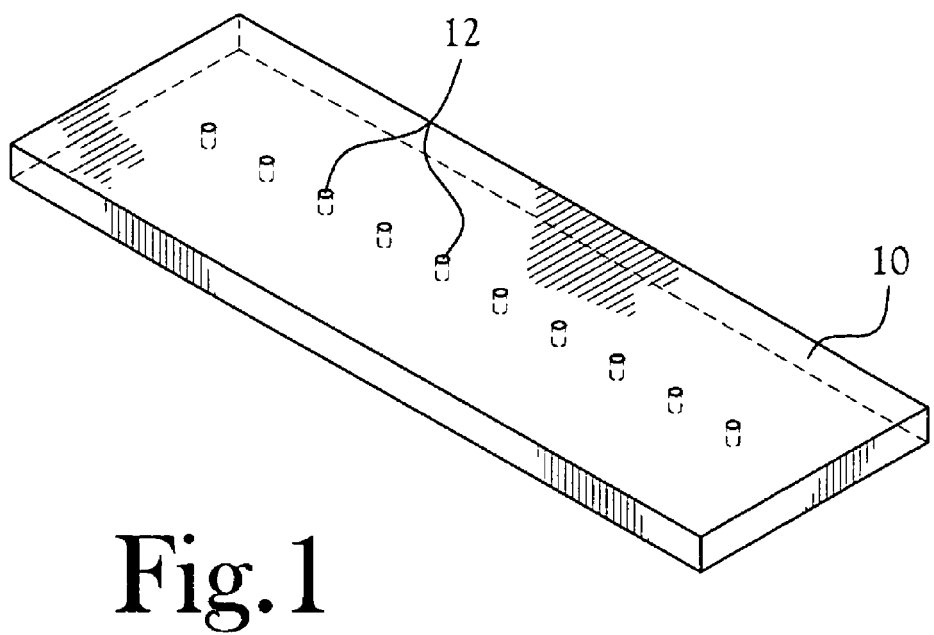
FIG. 1 is a perspective view of a device having a plurality of fiduciary markers fabricated in accordance with several features of the present invention.

FIG. 1 illustrates a device 10 having embedded markers 12 fabricated in accordance with the present invention. The markers of the illustrated embodiment are doped with at least two of a silicone-based polymer for use with an MRI device, a metal for use with an X-ray CT scanner, and a positron emitting nuclide for use with a PET scanner. The illustrated device 10 is fabricated from acrylic defining a thickness of approximately ⅛", with the embedded markers being spaced at about ¼" spacing.

Figure 2:
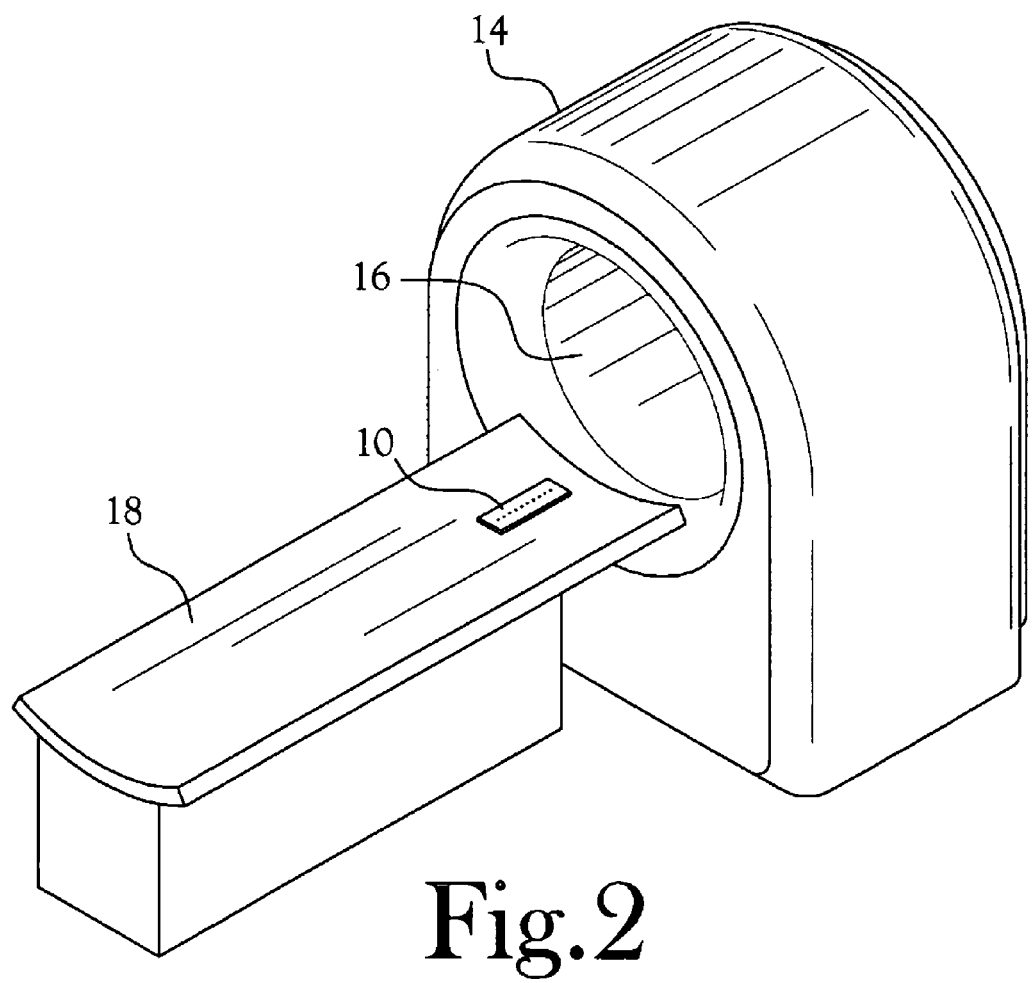
FIG. 2 is a perspective view of the device of FIG. 1 shown positioned within the patient gantry of an imaging device.

FIG. 2 illustrates the device of FIG. 1 being disposed on the patient bed. The patient bed is positioned within the patient gantry of an imaging device such that the device 10 is within the field of view of the imaging device. During a scan, it will be understood that the device 10 may be placed at any location within the field of view of the imaging device 14 without interfering with the subject (not shown) being scanned. Further, while the device 10 is shown resting on the patient bed 18, it will be understood by those skilled in the art that the device 10 may be carried under or formed integrally with the patient bed 18.

Figure 5:
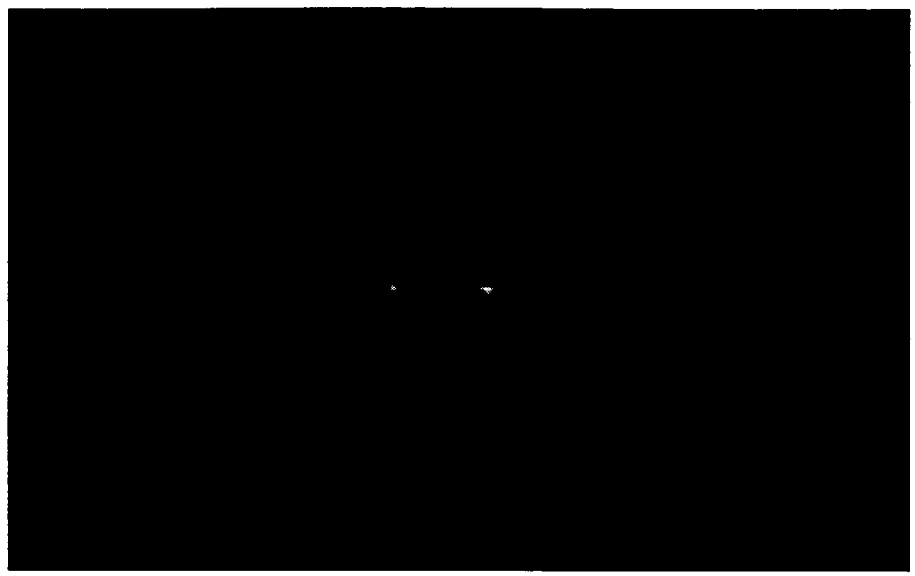
FIG. 5 is a data image of a scan of the fiduciary markers of FIG. 1 using PET.
Figure 4:
FIG. 4 is a data image of a scan of three fiduciary markers of FIG. 1 using CT.
Figure 3:
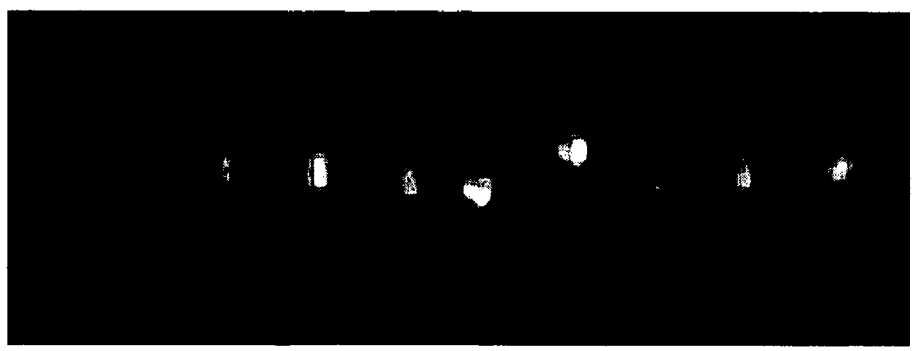
FIG. 3 is a data image of a scan of the fiduciary markers of FIG. 1 using MRI.

FIGS. 3-5 are data images of scan of the fiduciary markers 12 embedded in the device 10 using a conventional MRI device, a conventional X-ray CT device, and a conventional PET scanner. From the images acquired in FIGS. 3 and 5, it is seen that all of the markers are doped with a silicone-based polymer and a positron emitting nuclide. As seen in the image of FIG. 4, only three of the markers 12 are doped with a metal. Once the images have been acquired, common points on each image relating to the markers 12 are registered as described above.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, We claim:

1. A solid fiduciary marker for registering at least two images of a subject using at least two distinct imaging devices, each of the imaging devices defining a patient gantry configured to receive a patient bed, said solid fiduciary marker comprising:
    a substrate configured to be carried by the patient bed and within the patient gantry of each of the imaging devices when the patient bed is received therein; and
    at least one marker embedded within said substrate, said at least one marker being formed of a first material capable of functioning as a contrast agent for a first imaging modality, and said first material being doped with a second material that functions as a contrast agent for a second imaging modality different from said first imaging modality.

2. The solid fiduciary marker of claim 1 wherein the imaging devices are selected from the group consisting of at least a Positron Emission Tomography (PET) scanner; a Single Photon Emission Computed Tomography (SPECT) scanner; a planar gamma camera; an X-ray CT scanner; a planar X-ray device; a Magnetic Resonance Imaging (MRI) device; and an optical imager, and
    wherein said first material comprises a silicone-based polymer, and said second material is selected from the group consisting of at least a positron emitting nuclide for use with said PET scanner; a gamma emitting nuclide for use with at least one of said SPECT camera and said planar gamma camera; a metal for use in association with at least one of said X-ray CT scanner and said planar X-ray device; and a photostimulable phosphor for use in association with an optical imager.

3. The solid fiduciary marker of claim 1, wherein said first material is further doped with a third material that functions as a contrast agent for a third imaging modality different from said first and second imaging modalities.

4. The solid fiduciary marker of claim 3, wherein said first material comprises a silicone-based polymer, said second material is selected from the group consisting of a positron emitting nuclide, a gamma emitting nuclide, a metal, and a photostimulable phosphor, and said third material is selected from the remainder of said group.

5. The solid fiduciary marker of claim 4, wherein said first imaging modality is selected from the group consisting of PET, SPECT, nuclear planar imaging, X-ray CT, planar X-ray, and optical imaging, and said second imaging modality is selected from the remainder of said group.

6. The solid fiduciary marker of claim 1, wherein said first imaging modality is Magnetic Resonance Imaging (MRI) and said second imaging modality is selected from the group consisting of PET, SPECT, nuclear planar imaging, X-ray CT, planar X-ray, and optical imaging.

7. The solid fiduciary marker of claim 1, wherein said substrate is comprised of acrylic.

8. An imaging system for registering at least two images of a subject positioned on a patient support, said imaging system comprising:
- a first imaging device selected from the group consisting of at least a Positron Emission Tomography (PET) scanner; a Single Photon Emission Computed Tomography (SPECT) scanner; a planar gamma camera; an X-ray CT scanner; a planar X-ray device; a Magnetic Resonance Imaging (MRI) device; and an optical imager, said first imaging device defining a patient gantry for receipt of said patient support and the patient therein;
- a second imaging device selected from the remaining of the group consisting of at least a PET scanner; a SPECT scanner; a planar gamma camera; an X-ray CT scanner; a planar X-ray device; an MRI device; and an optical imager, said second imaging device defining a patient gantry for receipt of said patient support and the patient therein;
- a substrate configured to be carried by the patient bed and within the patient gantry of each of the imaging devices when the patient bed is received therein; and
- at least one solid marker embedded within said substrate, said at least one marker being formed of a first material capable of functioning as a contrast agent for a MRI device, and said first material being doped with a second material that functions as a contrast agent for one of said PET scanner; said SPECT scanner; said planar gamma camera; said X-ray CT scanner; said planar X-ray device; and said optical imager.

9. The imaging system of claim 8 wherein said first material comprises a silicone-based polymer, and said second material is selected from the group consisting of at least a positron emitting nuclide for use with said PET scanner; a gamma emitting nuclide for use with at least one of said SPECT camera and said planar gamma camera; a metal for use in association with at least one of said X-ray CT scanner and said planar X-ray device; and a photostimulable phosphor for use in association with an optical imager.

10. The imaging system of claim 8, wherein said substrate is comprised of acrylic.

* * * * *